United States Patent [19]

Edwards et al.

[11] Patent Number: 4,833,135
[45] Date of Patent: May 23, 1989

[54] ANTIOESTROGENIC PHENOL DERIVATIVES

[75] Inventors: Philip N. Edwards, Bramhall; Neil J. Hales, Macclesfield; Derek W. Young, Wilmslow, all of United Kingdom

[73] Assignee: Imperial Chemical Industries PLC, London, England

[21] Appl. No.: 726,822

[22] Filed: Apr. 24, 1985

[30] Foreign Application Priority Data

Apr. 27, 1984 [GB] United Kingdom ................. 8410899

[51] Int. Cl.$^4$ ..................... A61K 31/55; C07D 231/12
[52] U.S. Cl. ..................... 514/212; 514/218; 514/227.8; 514/228.2; 514/228.5; 514/234.2; 514/234.5; 514/235.2; 514/236.2; 514/236.5; 514/252; 514/253; 514/314; 514/319; 514/320; 514/322; 514/324; 514/326; 514/364; 514/406; 514/407; 540/544; 540/553; 540/575; 540/597; 540/603
[58] Field of Search ............... 548/336, 374, 126, 143, 548/144, 372, , 375, 378; 546/165, 177, 196, 199, 202, 206, 210, 211; 544/363, 364, 367, 368, 371, 128, 138, 140, 58.5, 58.6, 58.7; 540/544, 553, 575, 597, 603

[56] References Cited

U.S. PATENT DOCUMENTS 2,914,563 11/1959 Allen et al. ..................... 568/809

OTHER PUBLICATIONS

Ehrhardt/Ruschig "Arzneimittel", 2nd edition, vol. 3, 1972, Verlag Chemie, Weinheim, pp. 330, 331.

Primary Examiner—Richard A. Schwartz
Attorney, Agent, or Firm—Cushman, Darby & Cushman

[57] ABSTRACT

A phenol derivative of the formula

NU-A-X-R$^1$ wherein NU is a defined bis-phenolic nucleus including a hydroxyphenyl-hydroxynaphthyl; hydroxyphenyl-hydroxy-indanyl, hydroxyphenyl-hydroxybenzothienyl or di-hydroxyphenyl-ethylene or vinylene nucleus; wherein A is alkylene, alkenylene or cycloalkylene which is interrupted by a heterocyclene linkage, wherein R$^1$ is hydrogen, or alkyl, alkenyl, cycloalkyl, halogenoalkyl, aryl or arylalkyl, or R$^1$ is joined to R$^2$, and wherein X is —CONR$^2$—, —CSNR$^2$—, —NR$^1$$^2$CO—, —NR$^{12}$CS—, —NR$^{12}$CONR$^2$—, $$-NR^{12}-\overset{NR^{22}}{\underset{\|}{C}}-NR^2-,$$

—SO$_2$NR$^2$— or —CO—, or, when R$^1$ is not hydrogen, is —NR$^{12}$COO—, —S—, —SO— or —SO$_2$—, wherein R$^2$ is hydrogen or alkyl, or R$^1$ and R$^2$ together form alkylene; wherein R$^{12}$ is hydrogen or alkyl, and wherein R$^{22}$ is hydrogen, cyano or nitro; or a salt thereof when appropriate. The compounds possess antioestrogenic activity and may be used for the treatment of hormone-dependent breast tumors or of anovulatory infertility.

9 Claims, No Drawings

ANTIOESTROGENIC PHENOL DERIVATIVES

This invention relates to new phenol derivatives which possess antioestrogenic activity.

Various antioestrogens are now known. Two such compounds, tamoxifen and clomiphene, are commercially available, and others, for example nafoxidine, trioxifene and a number of compounds with code-numbers such as Cl 628 and LY 117018, have been the subject of clinical trials. Many oestrogenic compounds are also known, and in particular oestrogens based on hexoestrol bearing an amidic function, of the general formula:

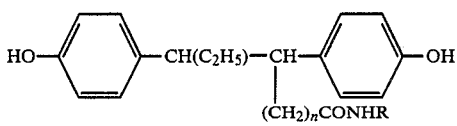

wherein n is 0 or 1 and R is hydrogen or alkyl, are described in the Journal of Medicinal Chemistry, 1982, 25, 1300-1307.

We have now found that certain phenol derivatives which are based on the hexoestrol nucleus but which bear an amidic or other function separated from the nucleus by an extended alkylene chain possess potent antioestrogenic activity.

According to the invention there is provided a phenol derivative of the formula:

where NU is a bis-phenolic nucleus of the general formula

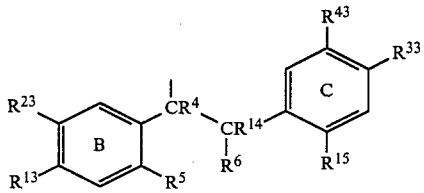

wherein one of $R^{13}$ and $R^{23}$, and one of $R^{33}$ and $R^{43}$, has the formula $R^3O-$, wherein each $R^3$, which may be the same or different, is hydrogen or alkyl, cycloalkyl, alkanoyl, alkoxycarbonyl, carboxyalkanoyl or aroyl each of up to 10 carbon atoms, and wherein the other of $R^{13}$ and $R^{23}$, and the other of $R^{33}$ and $R^{43}$, is hydrogen;
  wherein $R^4$ and $R^{14}$, which may be the same or different, each is hydrogen or alkyl of up to 5 carbon atoms, or $R^4$ and $R^{14}$ are joined together so that $CR^4$-$CR^{14}$ is an olefinic double bond;
  wherein either $R^5$ and $R^{15}$ are both hydrogen and $R^6$ is alkyl of up to 5 carbon atoms;
  or $R^5$ and $R^6$ together form a direct link or $-CH_2-$, $-CH(CH_3)-$, $-CH_2CH_2-$, $-(CH_2)_3-$, $-CH=CH-$, $-S-$, $-O-$, $-O-CR_2-$, $-O-CO-$, $-NR-CH_2-$ or $-N=CH-$ wherein the two values of R, which may be the same or different in $-OCR_2-$, is hydrogen or alkyl of up to 3 carbon atoms and $R^{15}$ is hydrogen;
  or $R^{15}$ and $R^6$ together form $-CH_2-$ and $R^5$ is hydrogen;

and wherein the aromatic rings B and C each may optionally bear one or more halogen or alkyl substituents; p1 wherein A has the formula:

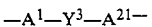

wherein $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^3$ is heterocyclene which may optionally bear one or more halogen, alkyl, alkoxy or oxo substituents, or A has the formula:

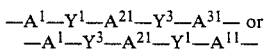

wherein $A^1$ and $A^{11}$ are each alkylene or alkenylene, and $A^{21}$ and $A^{31}$ are each a direct link or alkylene or alkenylene, such that $A^1$, $A^{21}$ and $A^{31}$ together, or $A^1$, $A^{21}$ and $A^{11}$ together, have a total of 1 to 9 carbon atoms, wherein $Y^1$ is $-O-$, $-S-$, $-SO-$, $-SO_2-$ or $-CO-$, and wherein $Y^3$ has the meaning stated above; wherein $R^1$ is hydrogen, or alkyl, alkenyl, cycloalkyl, halogenoalkyl, aryl or arylalkyl each of up to 10 carbon atoms, or $R^1$ is joined to $R^2$ as defined below; and wherein X is $-CONR^2-$, $-CSNR^2-$, $-NR^{12}CO-$, $-NR^{12}CS-$, $-NR^{12}CONR^2-$,

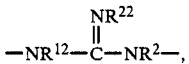

$-SO_2NR^2-$ or $-CO-$, or, when $R^1$ is not hydrogen, is $-NR^{12}COO-$, $-S-$, $-SO-$ or $-SO_2-$, wherein $R^2$ is hydrogen or alkyl of up to 6 carbon atoms, or $R^1$ and $R^2$ together form alkylene such that, with the adjacent nitrogen atom, they form a heterocyclic ring of 5 to 7 ring atoms, one of which may be a second heterocyclic atom selected from oxygen, sulphur and nitrogen; wherein $R^{12}$ is hydrogen or alkyl of up to 6 carbon atoms; and wherein $R^{22}$ is hydrogen, cyano or nitro; or a salt thereof when appropriate.

It will be observed that except when $R^4$ and $R^{14}$ are joined together so that $CR^4$-$CR^{14}$ is an olefinic double bond, the phenol derivative of the invention possesses at least two asymmetric carbon atoms, namely those which bear the substituents $R^4$ and $R^{14}$, and it can therefore exist in racemic and optically-active forms. It is to be understood that this invention encompasses any racemic form of the phenol derivative, and any optically active form thereof, which possesses antioestrogenic activity, it being a matter of common general knowledge how a racemic compound may be separated into its optically-active forms, and how the antioestrogenic properties of any such form may be determined.

A suitable value for the one or more optional halogen or alkyl substituent in ring B or C, or in the heterocyclene group $-Y^3-$, is, for example, fluoro, chloro, bromo, iodo, methyl or ethyl.

Preferably $R^{23}$ and $R^{43}$ are hydrogen and $R^{13}$ and $R^{33}$ have the formula $R^3O-$.

A suitable value for $R^3$ when it is cycloalkyl, alkanoyl, alkoxycarbonyl, carboxyalkanoyl or aroyl is, for example, cyclopentyl, formyl, acetyl, propionyl, butyryl, pivaloyl, decanoyl, isopropoxycarbonyl, succinyl, glutaryl or benzoyl. $R^3$ is preferably hydrogen or alkanoyl or alkoxycarbonyl each of up to 5 carbon atoms, especially hydrogen.

A suitable value for R, $R^3$, $R^4$ or $R^{14}$ when it is alkyl is, for example, methyl or ethyl. R and $R^4$ are preferably hydrogen and $R^{14}$ is preferably hydrogen or methyl, or R is hydrogen and $R^4$ and $R^{14}$ are joined together.

A suitable value for $R^6$ when it is alkyl is, for example, methyl, ethyl or n-propyl.

A preferred value for the group —A— is a group of the formula

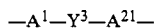

wherein $A^1$ is straight-chain alkylene or alkenylene each of 2 to 9 carbon atoms, especially alkylene of 3 to 6 carbon atoms, —$Y^3$— is heterocyclene and $A^{21}$ is a direct link, methylene, ethylene, trimethylene or vinylene, especially ethylene.

A suitable value for the heterocyclene group —$Y^3$— is, for example, a mono- or bi-cyclic divalent heterocyclic group which contains 1, 2 or 3 heteroatoms selected from nitrogen, oxygen and sulphur atoms, which may be fully saturated, partially saturated or unsaturated, which may be fused to a benzene ring, and which may bear one or more halogen, alkyl, alkoxy or oxo substituents. The free bonds may be attached to carbon atoms or nitrogen atoms. Particular heterocyclene groups are, for example, thien-2,5-ylene, thien-2,4-ylene, pyrazol-1,4-ylene, thiazol-2,5-ylene, 1,3,4-thiadiazol-2,5-ylene, 1,3,4-oxadiazol-2,5-ylene, piperidine-1,4-diyl and 1,4-piperazine-1,4-diyl.

A suitable alkoxy substituent in $Y^3$ is, for example, methoxy or ethoxy.

A suitable value for $R^1$ when it is alkyl, alkenyl or cycloalkyl is, for example, methyl, ethyl, n-propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, n-undecyl, allyl, cyclopentyl or cyclohexyl.

A suitable value for $R^1$ when it is aryl or aralkyl is, for example, phenyl, o-ethylphenyl, p-chlorophenyl, m-chlorophenyl, p-cyanophenyl, p-hydroxyphenyl, p-methoxyphenyl, benzyl, alpha-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl or p-chlorophenethyl.

A suitable value for $R^1$ when it is halogenoalkyl is, for example, 2-chloro-2,2-difluoroethyl, 2,2,2-trifluoroethyl, 1H,1H-heptafluorobutyl, 4,4,5,5,5-pentafluoropentyl or 1H,1H,2H,2H,3H,3H-heptafluorohexyl.

A suitable value for the heterocyclic ring —$NR^1R^2$ is, for example, pyrrolidino, piperidino, 4-methylpiperidino, 3-methylpiperidino, morpholino or 4-methylpiperazino.

A suitable value for $R^2$ or $R^{12}$ when it is alkyl is, for example, methyl, ethyl or n-butyl.

One appropriate salt is an acid-addition salt of a phenol derivative which possesses a basic function, for example a compound wherein $R^5$ and $R^6$ together form —NR—$CH_2$— or —N=CH—. A suitable acid-addition salt is, for example, a hydrochloride, hydrobromide, acetate, citrate, oxalate or tartrate.

Another appropriate salt is a base-addition salt of a phenol derivative which possesses a carboxy function, for example a compound wherein $R^3$ is carboxyalkanoyl. A suitable base-addition salt is, for example, a sodium, potassium, ammonium or cyclohexylamine salt.

A preferred phenol derivative of the invention has the formula stated above wherein both $R^3$ substituents and $R^{15}$ are all hydrogen, wherein either $R^4$ is hydrogen and $R^{14}$ is hydrogen, methyl or ethyl, or $R^4$ and $R^{14}$ are joined together, wherein either $R^5$ is hydrogen and $R^6$ is methyl, ethyl or n-propyl, or $R^5$ and $R^6$ together form —$CH_2$—, —$CH_2CH_2$—, —$CH(CH_3)$—, —CH=CH— or —S—, wherein —A— is

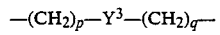

wherein p is an integer from 2 to 9, especially from 3 to 6, q is 0 to 3, especially 2, and $Y^3$ is pyrazol-1,4-ylene, 1,3,4-oxadiazol-2,5-ylene, piperidine-1,4-diyl or 1,4-piperazine-1,4-diyl; wherein $R^1$ is alkyl or fluoroalkyl each of 4 to 10 carbon atoms, especially of 4 to 7 carbon atoms, or phenyl or chlorophenyl, or alkyl of 1 to 3 carbon atoms which bears a phenyl, tolyl, halogenophenyl or trifluoromethylphenyl substituent, or is linked to $R^2$ as stated below; wherein X is —$CONR^2$—, —S—, —SO— or —$SO_2$—, wherein $R^2$ is hydrogen or alkyl of up to 3 carbon atoms or together with $R^1$ forms alkylene of 5 or 6 carbon atoms; and wherein ring C may optionally bear one or two methyl substituents.

A particularly preferred phenol derivative of the invention has the formula stated above wherein the number of carbon atoms in the two groups A (excluding those in the heterocylene group) and $R^1$ adds up to between 8 and 15, especially 11 to 13 if there is no phenyl group in $R^1$, and 13 to 15 if there is a phenyl group in $R^1$.

An especially preferred phenol derivative of the invention has the formula stated above wherein:

NU is 6-hydroxy-2-p-hydroxyphenylnaphth-1-yl and A is —$(CH_2)_5$—$Y^3$—$(CH_2)_2$—;

or NU is 1,2,3,4-tetrahydro-6-hydroxy-2-p-hydroxyphenylnaphthyl-1-yl (either 1RS, 2RS or 1RS, 2SR isomer), or 1,2,3,4-tetrahydro-6-hydroxy-2-p-hydroxyphenyl-2-methylnaphth-1-yl (either 1RS, 2RS or 1RS, 2SR isomer), and A is —$(CH_2)_4$—$Y^3$—$(CH_2)_2$— or —$(CH_2)_4$—$Y^3$—$(CH_2)_3$—;

or NU is (1RS, 2RS)-5-hydroxy-2-p-hydroxy-phenylindan-1-yl or (1RS, 2RS)-5-hydroxy-2-p-hydroxyphenyl-2-methylindan-1-yl and A is —$(CH_2)_4$—$Y^3$—$(CH_2)_2$—;

wherein —$Y^3$— is pyrazol-1,4-ylene, 1,3,4-oxadiazol-2,5-ylene, piperidine-1,4-diyl or 1,4-piperazine-1,4-diyl;

and wherein X is —$CONR^1R^2$ wherein $R^2$ is hydrogen or methyl and $R^1$ is n-butyl, 1H,1H-heptafluorobutyl, n-pentyl or n-hexyl, or X is —$SR^1$, $SOR^1$ or —$SO_2R^1$ wherein $R^1$ is n-pentyl, n-hexyl, 4,4,5,5,5-pentafluoropentyl or 1H,1H,2H,2H,3H,3H-heptafluorohexyl.

The most especially preferred value for NU is (1RS, 2RS)-1,2,3,4-tetrahydro-6-hydroxy-2-p-hydroxyphenyl-2-methylnaphth-1-yl, and the most especially preferred value for $Y^3$ is pyrazol-1,4-ylene.

Specific phenol derivatives of the invention are hereinafter described in the Examples. Of these, particularly preferred compounds are:

(1RS,2RS)-1-{4-[4-(2-n-hexylthioethyl)pyrazol-1-yl]butyl}-2-p-hydroxyphenyl-2-methyl-1,2,3,4-tetrahydronaphth-6-ol and the corresponding hexylsulphinyl derivative, and the corresponding 4,4,5,5,5-pentafluoropentylthio and 4,4,5,5,5-pentafluoropentylsulphinyl derivatives.

A preferred process for the manufacture of a phenol derivative of the invention wherein X has the formula —$CONR^2$—, —$CSNR^2$— or —$SO_2NR^2$— comprises the reaction of a compound of the formula $NU^1—A—Z^1$, wherein A has the meaning stated above, wherein $NU^1$ has the same meaning as stated above for NU except that the hydroxy groups are protected and wherein $Z^1$ is an activated group derived from a carboxylic, thiocarboxylic or sulphonic acid with an amine of the formula $HNR^1R^2$, wherein $R^1$ and $R^2$ have the meanings stated above, whereafter the protecting groups in $NU^1$ are removed by conventional means. A suitable activated group $Z^1$ is, for example, a mixed anhydride, for example an anhydride formed by reaction of the acid with a chloroformate such as isobutyl chloroformate.

A suitable protecting group in $NU^1$ is, for example, an alkyl or aralkyl ether, for example the methyl or benzyl ether, or a tetrahydropyranyl ether, of both of the hydroxy functions. The methyl ether is preferred, and the methyl group is preferably removed with boron tribromide.

A preferred process for the manufacture of a phenol derivative of the invention wherein X has the formula —CO— comprises the reaction of an acid of the formula $NU^1—A—COOH$, wherein $NU^1$ and A have the meanings stated above, with an organometallic compound of the formula $R^1—M$, wherein $R^1$ has the meaning stated above and M is a metal group, for example the lithium group, whereafter the protecting groups in $NU^1$ are removed by conventional means.

A preferred process for the manufacture of a phenol derivative of the invention wherein X has the formula —S— comprises the reaction of a compound of the formula $NU^1—A—Z^2$, wherein $NU^1$ and A have the meanings stated above and wherein $Z^2$ is a displaceable group, with a compound of the formula $R^1SH$, wherein $R^1$ has the meaning stated above, whereafter the protecting groups in $NU^1$ are removed by conventional means.

A suitable value for $Z^2$ is, for example, a halogen atom, for example the bromine atom, or a sulphonyloxy group, for example the methanesulphonyloxy or toluene-p-sulphonyloxy group.

A preferred process for the manufacture of a phenol derivative of the invention wherein X has the formula $—NR^{12}CO—$, $—NR^{12}CS—$, $—NR^{12}CONR^2—$, $$—NR^{12}—\overset{NR^{22}}{\underset{\|}{C}}—NR^2—$$

or $—NR^{12}COO—$ comprises the reaction of a compound of the formula $NU^1—A—NHR^{12}$, wherein $NU^1$, A and $R^{12}$ have the meanings stated above, with an acylating agent derived from an acid of the formula $R^1COOH$, $R^1CSOH$ or $R^1OCOOH$, or, for the manufacture of a urea, with an isocyanate of the formula $R^1NCO$; or, for the manufacture of a guanidine, with a cyanamide of the formula $R^1NR^2—CN$, whereafter the protecting groups in $NU^1$ are removed by conventional means.

A suitable acylating agent is, for example, an acyl chloride or acyl anhydride.

The starting materials for use in all the abovementioned processes may be obtained by elaborating the side-chain —A—COOH or $—A^2—CH_2OH$ onto the nucleus $NU^1$ by conventional means. Detailed methods for carrying out such an elaboration are hereinafter provided in the Examples, but in general terms a compound of the formula: $Z^2—A—COOR^7$ or $Z^2—A^2—CH_2OSi(CH_3)_2C(CH_3)_3$ or $HC\equiv C—A^{22}—CH_2OSi(CH_3)_2C(CH_3)_3$ wherein A and $Z^2$ have the meanings stated above, wherein $A^2$ is such that $—A^2CH_2—$ has the same meaning as A, wherein $A^{22}$ is such that $—CH_2CH_2A^{22}CH_2—$ has the same meaning as A, and wherein $R^7$ is hydrogen or alkyl of up to 6 carbon atoms, may be reacted with a suitable compound which is, or which may be converted into, $NU^1H$, or a compound of the formula:

$$NU^1—A^3—CHO$$

wherein $NU^1$ has the meaning stated above and wherein $A^3$ is a direct link or alkylene, may be reached with a diethylphosphonate of the formula:

$$(C_2H_5O)_2\overset{O}{\underset{\|}{P}}CH_2—A^4—COOR^7$$

or a triphenylphosphonium bromide of the formula:

$$(C_6H_5)_3P^+CH_2—A^4—COOR^7\ Br^-$$

wherein $R^7$ has the meaning stated above and $A^4$ is alkylene or modified alkylene, to provide a compound of the formula:

$$NU^1—A^3—CH=CH—A^4—COOR^7$$

wherein $NU^1$, $A^3$, $A^4$ and $R^7$ have the meanings stated above. This can be used directly to provide a phenol derivative of the invention wherein A contains an olefinic double bond, or it may be reduced to provide a starting material for the preparation of a phenol derivative of the invention wherein $—A^3—(CH_2)_2—A^4—$ has the same meaning as A defined above.

The intermediate of the formula $$NU^1—A^2—CH_2OH$$

wherein $NU^1$ and $A^2$ have the meanings stated above, may be oxidised to the corresponding carboxylic acid of the formula $NU^1—A^2—COOH$ which provides the starting material for the first or second process of the invention described above; or it may be converted into a compound of the formula $NU^1—A^2—CH_2Z^2$ by reaction with a halogenating agent or a sulphonylating agent to provide the starting material for the third process of the invention described above.

The starting material for the fourth process of the invention described above may be obtained by using the third process of the invention described above except that an amine of the formula $R^{12}NH_2$ is used in place of a thiol of the formula $R^1SH$.

A particularly preferred process for the manufacture of a phenol derivative of the invention comprises the reaction of a compound of the formula $$NU—A^1—Z^2 \text{ or } NU^1—A^1—Z^2$$

wherein NU, $NU^1$, $A^1$ and $Z^2$ have the meanings stated above, with a compound of the formula $$H—Y^3—A^{21}—X—R^1$$

wherein $R^1$, X, $A^{21}$ and $Y^3$ have the meanings stated above and wherein the H-atom is in a position in $—Y^3—$ such that $—Y^3—H$ can react with the compound $NU—A^1—Z^2$ or $NU^1—A^1—Z^2$, for example wherein the H-atom is attached to a nitrogen atom in —Y³—, whereafter the protecting groups in NU¹ are removed by conventional means.

A phenol derivative of the invention wherein either substituent $R^3$ is other than hydrogen may be obtained from the corresponding compound wherein either substituent $R^3$ is hydrogen by conventional etherification or esterification processes, and these may also be used in reverse to prepare the corresponding hydroxy compounds.

A phenol derivative of the invention wherein —X— is —CSNH— or —NHCS— may be obtained by the reaction of the corresponding compound wherein X is —CONH— or —NHCO— with 2,4-bis-(4-methoxyphenyl)-1,3-dithia-2,4-diphosphetane-2,4-disulphide.

A phenol derivative of the invention wherein X is —SO— or —SO$_2$— may be obtained by the oxidation of the corresponding compound wherein X is —S—. The conditions for the oxidation will be chosen to provide the desired product; for example aqueous sodium metaperiodate will oxidise the sulphur group to sulphinyl, and m-chloroperbenzoic acid in chloroform solution will oxidise the sulphur group to sulphonyl.

A phenol derivative of the invention wherein $R^5$ and $R^6$ form —CH$_2$CH$_2$— and either $R^4$ and $R^{14}$ are both hydrogen, or $R^4$ and $R^{14}$ are joined together so that $CR^4$—$CR^{14}$ is an olefinic double bond, may be converted into a phenol derivative of the invention wherein both —$CR^4$—$CR^{14}$— and —$R^5$—$R^6$— are —CH=CH— (that is, a naphthalene derivative) by aromatisation by conventional means, for example with 2,3-dichloro-5,6-dicyano-1,4-benzoquinone.

As stated above, a phenol derivative of the invention possesses antioestrogenic activity. This may be demonstrated by its effect in antagonising the increase in weight of the uterus of an immature female rat produced by administering oestradiol benzoate to said rat. Thus, when a phenol derivative of the invention and oestradiol benzoate are co-administered for 3 days to such a rat, a smaller increase in uterine weight is produced than the substantial increase which would be produced by the administration of oestradiol benzoate without the phenol derivative of the invention.

In particular, a preferred phenol derivative of the invention produces an antioestrogenic effect at a dose which produces no partial agonist effect, unlike the known antioestrogens tamoxifen and clomiphene. When a preferred phenol is coadministered with oestradiol benzoate to a rat as described above, no increase in uterine weight whatsoever is observed at a suitable dose.

A compound with the above pharmacological properties is of value in the treatment of the same conditions in which tamoxifen is beneficial, in particular, in the treatment of anovulatory infertility and in the treatment of breast tumours. It is also of value in the treatment of menstrual disorders.

When used to produce an anti-oestrogenic effect in warm-blooded animals, a typical daily dose is from 0.1 to 25 mg/kg. administered orally or by injection. In man this is equivalent to an oral dose of from 5 to 1250 mg./day. A phenol derivative of the invention is most conveniently administered to man in the form of a pharmaceutical composition.

According to a further feature of the invention, there is provided a pharmaceutical composition comprising a phenol derivative of the invention together with a pharmaceutically acceptable diluent or carrier.

The composition may be in a form suitable for oral or parenteral administration. A tablet or capsule is a particularly convenient form for oral administration and such a composition may be made by conventional methods and contain conventional excipients. Thus a tablet could contain diluents, for example mannitol or maize starch, disintegrating agents, for example alginic acid, binding agents, for example methyl-cellulose, and lubricating agents, for example magnesium stearate.

The composition may contain, in addition to the phenol derivative of the invention, one or more other agents which inhibit or antagonise hormonal action, for example antiandrogenic agents, for example flutamide, antiprogestational agents, or aromatase inhibition, for example aminoglutethimide.

A composition for oral administration may conveniently contain from 5 to 500 mg. of a phenol derivative of the invention.

The invention is illustrated but not limited by the following Examples:

EXAMPLE 1

A solution of 4-(2-hexylthioethyl)pyrazole (0.212 g.) in dimethylformamide (2 ml.) was added to a stirred suspension of sodium hydride (0.48 g. of a 50% dispersion in mineral oil from which the oil had been washed with petroleum ether) in dimethylformamide (10 ml.) and the mixture was stirred at laboratory temperature for 1 hour. A solution of (1RS,2RS)-1,2,3,4-tetrahydro-1-(4-mesyloxybutyl)-6-methoxy-2-p-methoxyphenyl-2-methylnaphthalene (0.432 g.) in dimethylformamide (10 ml.) was added and the mixture was stirred at laboratory temperature for 16 hours. Saturated aqueous sodium bicarbonate solution (30 ml.) was added and the mixture was extracted three times with methylene chloride (20 ml. each time). The combined extracts were dried and evaporated to dryness and the residue was purified by chromatography on a silica gel column using a 3:1 v/v mixture of petroleum ether (b.p. 60°–80° C.) and ethyl acetate as eluent.

A solution of boron tribromide (0.4 g.) in methylene chloride (3 ml.) was added to a stirred solution of the (1RS,2RS)-1-{4-[4-(2-hexylthioethyl)-pyrazol-1-yl]butyl}-1,2,3,4-tetrahydro-6-methoxy-2-p-methoxyphenyl-2-methylnaphthalene thus obtained in methylene chloride (10 ml.) which was cooled to −70° C. under an atmosphere of argon and the mixture was allowed to warm up to laboratory temperature and was then poured into saturated aqueous sodium bicarbonate solution (20 ml.). The mixture was extracted three times with methylene chloride (10 ml. each time) and the combined extracts were washed with water, dried and evaporated to dryness. The residue was purified by chromatography on a silica gel column using a 6:1 v/v mixture of methylene chloride and ethyl acetate as eluent. There was thus obtained as an oil (1RS,2RS)-1-{4-[4-(2-hexylthioethyl)pyrazol-1-yl]butyl}-1,2,3,4-tetrahydro-2-p-hydroxyphenyl-2-methylnaphth-6-ol, the structure of which was confirmed by proton magnetic resonance and mass spectroscopy.

The 4-(2-hexylthioethyl)pyrazole used as starting material was obtained as follows:

Hexanethiol (1.14 g.) was added to a stirred suspension of sodium hydride (0.48 g. of a 50% dispersion in mineral oil from which the oil had been washed with petroleum ether) in dimethylformamide (10 ml.) and the mixture was stirred at laboratory temperature for 1 hour. A solution of 4-(2-chloroethyl)pyrazole hydrochloride (0.835 g.; Journal of the American Chemical Society, 1953, 75, 4048) in dimethylformamide (10 ml.) was added and the mixture was stirred at laboratory temperature for 16 hours. Water (30 ml.) was added and the mixture was extracted three times with ethyl acetate (20 ml. each time). The combined extracts were dried and evaporated to dryness and the residue was purified by chromatography as a silica gel column using a 1:1 v/v mixture of ethyl acetate and toluene as eluent. There was thus obtained 4-(2-hexylthioethyl)pyrazole.

The (1RS,2RS)-1,2,3,4-tetrahydro-1-(4-mesyloxybutyl)-6-methoxy-2-p-methoxyphenyl-2-methylnaphthalene used as starting material was obtained as follows:

A solution of phosphorus oxychloride (0.2 ml.) in methylene chloride (15 ml.) was added slowly to a stirred solution of but-3-yn-1-ol (52.5g.) and 1H-3,4-dihydropyran (64 g.) in methylene chloride (120 ml.) which was cooled to 0° C., and the mixture was stirred at that temperature for 30 minutes. Diethyl ether (120 ml.) was added and the mixture was washed twice with saturated aqueous sodium bicarbonate solution (50 ml. each time) and once with saturated aqueous sodium chloride solution (50 ml.), dried and evaporated to dryness. The residue was distilled at 80°-86° C./10 mm.Hg. and further purified by chromatography through an alumina column. There was thus obtained but-3-yn-1-yl tetrahydropyran-2-yl ether.

A solution of 3,4-dihydro-6-methoxy-2-p-methoxyphenylnaphthalen-1(2H)-one (14.4 g.) in tetrahydrofuran (200 ml.) was added to a stirred solution of lithium diisopropylamide in tetrahydrofuran [prepared from n-butyllithium (31 ml. of a 1.6 molar solution in hexane ) and a solution of diisopropylamine (5.1 g.; freshly distilled from potassium hydroxide) in tetrahydrofuran (50 ml.)]which was cooled to -60° C. under an atmosphere of argon. The mixture was stirred at −60° C. for 30 minutes, methyl iodide (7 g.) was added and the mixture was stirred at laboratory temperature for 12 hours and then poured into saturated aqueous ammonium chloride solution (600 ml.). The mixture was extracted three times with ethyl acetate (100 ml. each time) and the combined extracts were washed with water, dried and evaporated to dryness. The residue was purified by chromatography on a silica gel column using a 9:1 v/v mixture of petroleum ether (b.p. 60°-80° C.) and ethyl acetate as eluent. There was thus obtained 3,4-dihydro-6-methoxy-2-p-methoxyphenyl-2-methylnaphthalen-1(2H)-one, m.p. 76°-78° C.

n-Butyllithium (40 ml. of a 1.65 molar solution in hexane) was added dropwise to a stirred solution of but-3-yn-1-yl tetrahydropyran-2-yl ether (11 g.) in tetrahydrofuran (200 ml.) which was cooled to 0° C. under an atmosphere of argon, and a solution of the above naphthalenone (9 g.) in tetrahydrofuran (100 ml.) was added. The mixture was stirred at laboratory temperature for 2 hours and then poured into ice-cold, saturated aqueous ammonium chloride solution (300 ml.) The mixture was extracted three times with ethyl acetate (100 ml. each time) and the combined extracts were washed with water, dried and evaporated to dryness. The residue was stirred with petroleum ether (b.p. 60°-80° C.) and the mixture was filtered. There was thus obtained 1,2,3,4-tetrahydro-6-methoxy-2-p-methoxyphenyl-2-methyl-1-(4-tetrahydropyran-2-yloxybut-3-yn-1-yl)naphth-1-ol.

A solution of the above naphthol (10 g.) in ethyl acetate (250 ml.) was stirred in an atmosphere of hydrogen for 90 minutes in the presence of a 10% palladium-on-charcoal catalyst (3 g.). The mixture was filtered, fresh catalyst (3 g.) was added to the filtrate and the mixture was stirred in an atmosphere of hydrogen for a further 90 minutes and then filtered. The filtrate was evaporated to dryness and the residue was purified by chromatography on silica gel column using a 10:1 v/v mixture of toluene and ethyl acetate as eluent. There was thus obtained an an oil (1RS, 2RS)-1,2,3,4-tetrahydro-6-methoxy-2-p-methoxyphenyl-2-methyl- (4-tetrahydropyran-2-yloxybutyl)naphthalene.

Aqueous 2N-hydrochloric acid (50 ml.) was added to a stirred solution of the above compound (6.8 g.) in ethanol (200 ml.), and the mixture was stirred and heated under reflux for 2 hours, cooled and evaporated to dryness. Saturated aqueous sodium bicarbonate solution (100 ml.) was added to the residue, and the mixture was extracted three times with ethyl acetate (100 ml. each time). The combined extracts were washed with water, dried and evaporated to dryness and the residue was purified by chromatography on a silica gel column using a 5:1 v/v mixture of toluene and ethyl acetate as eluent. There was thus obtained as an oil 4-[(1RS, 2RS)-6-methoxy-2-p-methoxyphenyl-2-methyl-1,2,3,4- tetrahydronaphth-1-yl]butan-1-ol.

A solution of the above butanol (0.5 g.) in methylene chloride (10 ml.) was cooled to 5° C. and pyridine (0.09 g.) and methanesulphonyl chloride (mesyl chloride; 0.21 g.) were successively added. The mixture was allowed to warm up to laboratory temperature and was stirred for 16 hours. Aqueous 2N-hydrochloric acid (15 ml.) was added, the mixture was extracted three times with methylene chloride (15 ml. each time) and the combined extracts were dried and evaporated to dryness. The residue was purified by chromatography on a silica gel column using a 10:1 v/v mixture of toluene and ethyl acetate as eluent and there was thus obtained (1RS, 2RS)-1,2,3,4-tetrahydro-1-(4-mesyloxybutyl)-6-methoxy-2-p-methoxyphenyl-2-methylnaphthalene.

EXAMPLE 2

A solution of sodium metaperiodate (0.1 g.) in water (2 ml.) was added to a stirred solution of (1RS,2RS)-1-{4-[4-(2-hexylthioethyl)pyrazol-1-yl]butyl}-1,2,3,4-tetrahydro-2-p-hydroxyphenyl-2-methylnaphth-6-ol (Example 1; 0.23 g.) in a mixture of methanol (4 ml.) and tetrahydrofuran (4 ml.) and the mixture was stirred at laboratory temperature for 16 hours, diluted with water (20 ml.) and extracted three times with methylene chloride (10 ml. each time). The combined extracts were dried and evaporated to dryness and the residue was purified by chromatography on a silica gel column using a 49:1 v/v mixture of ethyl acetate and ethanol as eluent. There was thus obtained as an oil (1RS,2RS)-1-{4-[4-(2-hexylsulphinylethyl)pyrazol-1-yl]butyl}-1,2,3,4-tetrahydro-2-p-hydroxyphenyl-2-methylnaphth-6-ol.

EXAMPLE 3

The process described in the first paragraph of Example 1 was repeated except that 4-[2-(1H,1H,2H,2H,3H,3H-heptafluorohexylthio)ethyl]-pyrazole was used as starting material in place of the corresponding hexylthioethylpyrazole. The product obtained was demethylated with boron tribromide as described in the second paragraph of Example 1, and the product of this reaction was oxidised with sodium metaperiodate as described in Example 2. There were thus obtained as oils, successively: (1RS,2RS)-1-{4-[4-(2-{1H, 1H,2H, 2H,3H,3H-heptafluorohexylthio}ethyl)pyrazol-1-yl]butyl}-1,2,3,4-tetrahydro-6-methoxy-2-p-methoxyphenyl-2-methylnaphthalene;

[1RS,2RS)-1-{4-[4-(2-{1H,1H,2H,2H,3H,3H-heptafluorohexylthio}ethyl)pyrazol-1-yl]butyl}-1,2,3,4-tetrahydro-2-p-hydroxyphenyl-2-methylnaphth-6-ol; and (1RS,2RS)-1-{4-[4-(2-{1H,1H,2H,2H,3H,3H-heptafluorohexylsulphinyl}ethyl)pyrazol-1-yl]butyl}-1,2,3,4-tetrahydro-2-p-hydroxyphenyl-2-methylnaphth-6-ol, the structures of all of which were confirmed by proton magnetic resonance and mass spectroscopy.

The pyrazole starting material was obtained by a similar process to that described in the third paragraph of Example 1, except that S-(1H,1H,2H,2H,3H,3H-heptafluorohexyl)isothiouronium p-toluenesulphonate and aqueous sodium hydroxide solution were used as starting materials in place of hexanethiol and sodium hydride.

EXAMPLE 4

A solution of $N^1$-{5-[(1RS,2RS)-6-methoxy-2-p-methoxyphenyl-2-methyl-1,2,3,4-tetrahydronaphth-1-yl]-valeryl}-$N^2$-(3-hexylthiopropionyl)hydrazine (0.2 g.) and p-toluenesulphonic acid (0.05 g.) in toluene (25 ml.) was heated under reflux for 3 hours in a Dean and Stark water-separating apparatus, cooled, washed successively with water, saturated aqueous sodium bicarbonate solution and water, dried over magnesium sulphate and evaporated to dryness. The residue was purified by chromatography on a silica gel column using a 3:1 v/v mixture of toluene and ethyl acetate as eluent.

A molar solution of boron tribromide in methylene chloride (1 ml.) was added to a stirred solution of the (1RS,2RS)-1-{4-[5-(2-hexylthioethyl)-1,3,4-oxadiazol-2-yl]butyl}-1,2,3,4-tetrahydro-6-methoxy-2-p-methoxyphenyl-2-methylnaphthalene thus obtained in methylene chloride (15 ml.) which was cooled to −70° C. under an atmosphere of argon, and the mixture was allowed to warm up to laboratory temperature and was then poured into saturated aqueous sodium bicarbonate solution. The phases were separated and the aqueous phase was extracted with methylene chloride. The combined methylene chloride solutions were washed with water and then with saturated aqueous sodium chloride solution, dried and evaporated to dryness. The residue was purified by chromatography on a silica gel column using a 3:1 v/v mixture of toluene and ethyl acetate as eluent. There was thus obtained as an oil (1RS,1RS)-1-{4-[5-(2-hexylthioethyl)-1,3,4-oxadiazol-2-yl]butyl}-1,2,3,4-tetrahydro-2-p-hydroxyphenyl-2-methylnaphth-6-ol, the structure of which was confirmed by proton magnetic resonance and mass spectroscopy.

The $N^1$-{5-[(1RS,2RS)-6-methoxy-2-p-methoxyphenyl-2-methyl-1,2,3,4-tetrahydronaphth-1-yl]valeryl}($N^2$-(3-hexylthiopropionyl)hydrazine used as starting material was obtained as follows:

A mixture of (1RS,2RS)-1,2,3,4-tetrahydro-1-(4-mesyloxybutyl)-6-methoxy-2-p-methoxyphenyl-2-methylnaphthalene (Example 1, 1.73 g.), potassium cyanide (0.4 g.) and dimethylsulphoxide (13 ml.) was stirred for 5 hours at 90° C. under an atmosphere of argon and then poured into saturated aqueous sodium chloride solution, and the mixture was extracted with ethyl acetate. The extract was dried and evaporated to dryness and a solution of the 5-[(1RS,2RS)-6-methoxy-2-p-methoxyphenyl-2-methyl-1,2,3,4-tetrahydronaphth-1-yl]valeronitrile thus obtained as residue (2.5 g.) and powdered potassium hydroxide (2.5 g.) in a mixture of ethane-1,2-diol (25 ml.) and water (2.5 ml.) was heated at 180° C. for 3½ hours and then added to a mixture of ice and water. The mixture was washed with diethyl ether and the aqueous phase was acidified with aqueous 3N-hydrochloric acid and extracted with diethyl ether. The extract was dried and evaporated to dryness and a mixture of the 5-[(1RS,2RS)-6-methoxy-2-p-methoxyphenyl-2-methyl-1,2,3,4-tetrahydronaphth-1-yl]valeric acid thus obtained as residue (0.457 g.), oxalyl chloride (0.15 ml.), dimethyl formamide (1.01 ml.) and methylene chloride (20 ml.) was stirred at laboratory temperature for 2 hours and then evaporated to dryness. A solution of the residue thus obtained in methylene chloride (10 ml.) was added to a stirred solution of 3-hexylthiopropionohydrazide (0.242 g.) and triethylamine (0.15 ml.) in methylene chloride (15 ml.) and the mixture was kept at laboratory temperature for 1 hour. The reaction mixture was washed with water, dried and evaporated to dryness and the residue was purified by chromatography on a silica gel column using a 1:1 v/v mixture of toluene and ethyl acetate as eluent. There was thus obtained as an oil $N^1$-{b 5-[(1RS,2RS)-6-methoxy-2-p-methoxyphenyl-2-methyl-1,2,3,4-tetrahydronaphth-1-yl]valeryl}-$N^2$-(3-hexylthiopropionyl)hydrazine.

The 3-hexylthiopropionohydrazide used as starting material was obtained as follows: Hexanethiol (21.1 ml.) was added dropwise to a stirred mixture of a solution of 3-bromopropionic acid (15.3 g.) in warm isopropanol (200 ml.) and a solution of sodium hydroxide (10 g.) in water (30 ml.) and the reaction mixture was heated under reflux for 24 hours and then evaporated to dryness under reduced pressure. The residue was acidified with aqueous 2N-hydrochloric acid and extracted three times with petroleum ether (b.p. 60°-80° C.). The extracts were combined, washed three times with water and once with saturated aqueous sodium chloride solution, dried and evaporated to dryness. The residue was dissolved in diethyl ether and the solution was extracted with aqueous 2N-sodium hydroxide solution. The basic aqueous solution was washed with diethyl ether, acidified and extracted three times with diethyl ether. The combined diethyl ether extracts were washed with water, dried and evaporated to dryness.

A solution of the 3-hexylthiopropionic acid thus obtained and concentrated sulphuric acid (0.1 ml.) in ethanol (100 ml.) was heated under reflux for 17 hours and then evaporated to dryness. A solution of the residue in diethyl ether was washed with aqueous sodium hydroxide and then with saturated aqueous sodium chloride solution, dried and evaporated to dryness.

A solution of the ethyl 3-hexylthiopropionate thus obtained as residue (4.0 g.) and hydrazine hydrate (1 ml.) in methanol (25 ml.) was heated under reflux for 2 hours and then evaporated to dryness. The residue was washed with petroleum ether (b.p. 60°-80° C.) and dried. There was thus obtained 3-hexylthiopropionohydrazide which was used without purification.

EXAMPLE 5

A mixture of (1RS,2RS)-1-(4-bromobutyl)-2-p-hydroxyphenyl-2-methyl-1,2,3,4-tetrahydronaphth-6-ol (0.25 g.), 4-(2-pentylthioethyl)piperazine hydrobromide (0.105 g.), sodium hydrogen carbonate (0.16 g.) and ethanol (5 ml.) was heated under reflux for 17 hours and then evaporated to dryness. The residue was purified by chromatography on a silica gel column using a 19:1 v/v mixture of methylene chloride and methanol as eluent. A solution of the (1RS,2RS)-1-{4-[4-(2-pentylthioethyl)-piperazin-1-yl]butyl}-2-methyl-2-p-hydroxyphenyl-1,2,3,4-tetrahydronaphth-6-ol thus obtained (0.11 g.) and sodium metaperiodate (0.04 g.) in a mixture of methanol (5 ml.) and water (0.5 ml.) was stirred at laboratory temperature for seventeen hours and then evaporated to dryness, and the residual solid was purified by chromatography on a silica gel column using a 9:1 v/v mixture of methylene chloride and methanol as eluent. There was thus obtained as an oil (1RS,2RS)-1-{4-[4-(2-pentylsulphinylethyl)piperazin-1-yl]butyl}-2-methyl-2-p-hydroxyphenyl-1,2,3,4-tetrahydronaphth-6-ol, the structure of which was confirmed by proton magnetic resonance and mass spectroscopy.

The (1RS,2RS)-1-(4-bromobutyl)-2-p-hydroxyphenyl-2-methyl-1,2,3,4-tetrahydronaphth-6-ol used as starting material was obtained as follows:

A molar solution of boron tribromide in methylene chloride (27.6 ml.) was added to a stirred solution of (1RS,2RS)-1,2,3,4-tetrahydro-1-(4-mesyloxybutyl)-6-methoxy-2-p-methoxyphenyl-2-methylnaphthalene (Example 1; 2.3 g.) in methylene chloride (30 ml.) which was cooled to −60° C. under an atmosphere of argon, and the mixture was allowed to warm up to laboratory temperature and then poured into iced water. The mixture was extracted with ethyl acetate and the extract was dried and evaporated to dryness. The residue was purified by chromatography on a silica gel column using a 9:1 v/v mixture of toluene and ethyl acetate as eluent. There were thus separately obtained the (1RS,2RS)- and (1RS,2SR)-isomers of 1-(4-bromobutyl)-2-p-hydroxyphenyl- 2-methyl-1,2,3,4-tetrahydronaphth-6-ol.

The 4-(2-pentylthioethyl)piperazine hydrobromide used as starting material was obtained as follows:

A mixture of 1-benzyloxycarbonylpiperazine (11.0 g.), 2-bromoethanol (6.3 g.), sodium hydrogen carbonate (4.2 g.), and ethanol (100 ml.) was heated under reflux for 16 hours and then evaporated to dryness and the residue was purified by chromatography on a silica gel column using a 9:1 v/v mixture of methylene chloride and methanol as eluent.

A solution of the 2-(4-benzyloxycarbonylpiperazin-1-yl)ethanol thus obtained (10.0 g.) in pyridine (100 ml.) was treated at 5° C. with p-toluenesulphonyl chloride (14.5 g). and the mixture was kept at that temperature for 17 hours and then poured into iced water. The mixture was extracted with ethyl acetate and the extract was washed with water and then with saturated aqueous sodium chloride solution, dried and evaporated to dryness. The residual oil was stirred with a mixture of ethyl acetate and petroleum ether (b.p. 60°-80° C.) and the solvent was decanted off.

2-(4-benzyloxycarbonylpiperazin-1-yl)ethyl p-toluenesulphonate thus obtained (1.6 g.) was added to a stirred mixture of pentanethiol (0.38 g.), sodium hydride (0.178 g. of a 50% dispersion in oil) and dimethylformamide (10 ml.) under an atmosphere of argon, and the mixture was stirred at laboratory temperature for 17 hours and then evaporated to dryness. Water was added to the residue and the mixture was extracted with ethyl acetate. The extract was washed with water and then with saturated aqueous sodium chloride solution, dried, and evaporated to dryness. The residue was purified by chromatography on a silica gel column using ethyl acetate as eluent.

A solution of the 1-benzyloxycarbonyl-4-(2-pentylthioethyl)piperazine thus obtained in a 48% v/v solution of hydrogen bromide in acetic acid (3 ml.) was stirred at laboratory temperature for 17 hours and then evaporated to dryness. The residue was stirred with diethyl ether and the solvent was decanted off. There was thus obtained as residue 4-(2-pentylthioethyl)piperazine hydrobromide.

EXAMPLE 6

The process described in Example 5 was repeated using the appropriate (1RS,2RS)- or (1RS,2SR)-isomer of 1-(4-bromobutyl)-2-p-hydroxyphenyl-2-methyl-1,2,3,4-tetrahydronaphth-6-ol and the appropriate cyclic amine as starting materials. There were thus obtained as oils the compounds described in the following Table, the structures of all of which were confirmed by proton magnetic resonance and mass spectroscopy:

| Het | m | X | R$^1$ | Stereochemistry |
|---|---|---|---|---|
| −N(CH$_2$CH$_2$)N− | 2 | SO | (CH$_2$)$_3$C$_2$F$_5$ | (1RS,2RS) |
| −N(CH$_2$CH$_2$)N− | 3 | −CON(CH$_3$)− | n-butyl | (1RS,2SR) |
| −N(CH$_2$CH$_2$)CH− | 3 | −CON(CH$_3$)− | n-butyl | (1RS,2RS) |

The cyclic amine starting materials were obtained as follows:

4-[2-(4,4,5,5,5-Pentafluoropentylsulphinyl)ethyl]piperazine hydrobromide was obtained as described in Example 5 using S-(4,4,5,5,5-pentafluoropentyl)isothiouronium p-toluenesulphonate and aqueous sodium hydroxide solution as starting materials in place of pentanethiol and sodium hydride.

N-n-Butyl-N-methyl-4-(piperazin-1-yl)butyramide was obtained as follows:

A mixture of 1-benzyloxycarobnylpiperazine (0.44 g.), ethyl 4bromobutyrate (0.39 g.), sodium hydrogen carbonate (0.168 g.) and ethanol (5 ml.) was heated under reflux for 17 hours and then evaporated to dryness. The residue was purified by chromatography on a silica gel column using ethyl acetate as eluent. A mixture of the ethyl 4-(4-benzyloxycarbonylpiperazin-1-yl)butyrate thus obtained (0.396 g.) and a solution of potassium hydroxide (0.067 g.) in water (1 ml.) was diluted with ethanol until a homogeneous solution was obtained and the solution was heated under reflux for 1 hour and then evaporated to dryness. A solution of the residue in water was washed with ethyl acetate, neutralised with aqueous 2N-hydrochloric acid and evaporated to dryness. The residue was extracted with methanol and the methanolic solution was evaporated to dryness. There was thus obtained as an oil 4-(4-benzyloxycarbonylpiperazin-1-yl)butyric acid.

A solution of this butyric acid (4.6 g.) and oxalyl chloride (3.9 ml.) in methylene chloride (13 ml.) was stirred at laboratory temperature until the evolution of gas was complete. The mixture was evaporated to dryness and to a solution of the residue in methylene chloride was added at 5° C. N-n-butyl-N-methylamine (15 ml.). The mixture was kept at laboratory temperature for 17 hours and then evaporated to dryness. The residue was stirred with diethyl ether, the mixture was filtered and the filtrate was evaporated to dryness. The residue was purified by chromatography on a silica gel column using a 9:1 v/v mixture of ethyl acetate and methanol as eluent.

A mixture of the N-n-butyl-N-methyl-4-(4- benzyloxycarbonylpiperazin-1-yl)butyramide thus obtained (0.187 g.), a 10% palladium-on-charcoal catalyst (0.1 g.) and ethanol (5 ml.) was stirred at laboratory temperature under an atmosphere of hydrogen for 22 hours and then filtered and the filtrate was evaporated to dryness. There was thus obtained as an oil N-n-butyl-N-methyl-4-(piperazin-1-yl)butyramide.

N-n-Butyl-N-methyl-4-(piperidin-4-yl)butyramide was obtained as follows:

A mixture of 4-(pyrid-4-yl)butyric acid hydrochloride (3.3 g.), oxalyl chloride (4 ml.) and methylene chloride (30 ml.) was stirred at laboratory temperature until the evolution of gas had ceased, and was then evaporated to dryness. To a solution of the residue in methylene chloride (30 ml.) at 5° C. was added N-n-butyl-N-methylamine (10 ml.) and the mixture was stirred at laboratory temperature for 17 hours, diluted with methylene chloride, washed with water, dried and evaporated to dryness. The residue was purified by chromatography on a silica gel column using a 19:1 mixture of methylene chloride and methanol as eluent.

A mixture of the N-n-butyl-N-methyl 4-pyrid-4-ylbutyramide thus obtained (2.2 g.), platinum oxide (0.2 g.) and acetic acid (50 ml.) was heated at 60° C. under an atmosphere of hydrogen at a pressure of 60 p.s.i. for 17 hours. and then evaporated to dryness. The residue was purified by chromatography on a silica gel column using a 4:1 v/v mixture of methylene chloride and methanol as eluent. There was thus obtained as an oil N-n-butyl-N-methyl-4-(piperidin-4-yl) butyramide.

What is claimed is:
1. A phenol derivative of the formula:

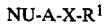
NU-A-X-$R^1$ where NU is a bis-phenolic nucleus of the general formula

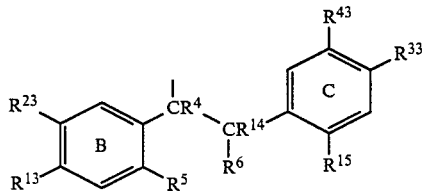

wherein one of $R^{13}$ and $R^{23}$, and one of $R^{33}$ and $R^{43}$, has the formula $R^3O-$, wherein each $R^3$, which may be the same or different, is hydrogen or alkyl, cycloalkyl, alkanoyl, alkoxycarobnyl, carboxyalkanoyl or aroyl each of up to 10 carbon atoms, and wherein the other of $R^{13}$ and $R^{23}$, and the other of $R^{33}$ and $R^{43}$, is hydrogen;

wherein $R^4$ and $R^{14}$, which may be the same or different, each is hydrogen or alkyl of up to 5 carbon atoms, or $R^4$ and $R^{14}$ are joined together so that $CR^4$-$CR^{14}$ is an olefinic double bond;

wherein either $R^5$ and $R^{15}$ are both hydrogen and $R^6$ is alkyl of up to 5 carbon atoms;

or $R^5$ and $R^6$ together form a direct link or $-CH_2-$, $-CH(CH_3)-$, $-CH_2-CH_2-$, $-(CH_2)_3-$, $-CH=CH-$, $-S-$, $-O-$, $-O-CR_2-$, $-O-CO-$, $-NR-CH_2-$ or $-N=CH-$ wherein R, the two values of which may be the same or different in $-OCR_2-$, is hydrogen or alkyl of up to 3 carbon atoms and $R^{15}$ is hydrogen;

or $R^{15}$ and $R^6$ together form $-CH_2-$ and $R^5$ is hydrogen;

and wherein the aromatic rings B and C each may optionally bear one or more halogen or alkyl substituents;

wherein A has the formula:

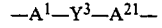
$-A^1-Y^3-A^{21}-$ wherein $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^3$ is mono- or bi-cyclic divalent heterocyclene consisting of at least one 5-membered heterocylic ring having two ring nitrogen atoms, which ring may be fused to a benzene ring and which may optionally bear one or more halogen, alkyl, alkoxy or oxo substituents, or A has the formula: 13 Ahu 1—$Y^1-A^{21}-Y^3-A^{31}-$ or $-A^1-Y^3-A^{21}-Y^1-A^{11}-$ wherein $A^1$ and $A^{11}$ are each alkylene or alkenylene, and $A^{21}$ and $A^{31}$ are each a direct link or alkylene or alkenylene, such that $A^1$, $A^{21}$ and $A^{31}$ together, or $A^1$, $A^{21}$ and $A^{11}$ together, have a total of 1 to 9 carbon atoms, wherein $Y^1$ is $-O-$, $-S-$, $-SO-$, $-SO_2$ or $-CO-$, and wherein $Y^3$ has the meaning stated above; wherein $R^1$ is hydrogen, or alkyl, alkenyl, cycloalkyl, halogenoalkyl, aryl or arylalkyl each of up to 10 carbon atoms, or $R^1$ is joined to $R^2$ as defined below; and wherein X is $-CONR^2$, $-CSNR^2-$, $-NR^{12}CO-$, $-NR^{12}CS-$, $-NR^{12}CONR^2-$, $$-NR^{12}-\overset{NR^{22}}{\underset{\|}{C}}-NR^2-,$$

$-SO_2NR^2-$ or $-CO-$, or, where $R^1$ is not hydrogen, is $-NR^{12}COO-$, $-S-$, $-SO-$ or $-SO_2-$, wherein $R^2$ is hydrogen or alkyl of up to 6 carbon atoms, or $R^1$ and $R^2$ together form alkylene such that, with the adjacent nitrogen atom, they form a heterocyclic ring of 5 to 7 ring atoms, one of which may be a second heterocyclic atom selected from oxygen, sulphur and nitrogen; wherein $R^{12}$ is hydrogen or alkyl of up to 6 carbon atoms; and wherein $R^{22}$ is hydrogen, cyano or nitro; or a salt thereof when appropriate.

2. A phenol derivative as claimed in claim 1 wherein $R^{15}$, $R^{23}$ and $R^{43}$ are all hydrogen; wherein $R^{13}$ and $R^{33}$ both have the formula $R^3O-$ wherein $R^3$ is hydrogen or alkanoyl or alkoxycarbonyl each of up to 5 carbon atoms; wherein either $R^4$ is hydrogen and $R^{14}$ is hydrogen, methyl or ethyl, or $R^4$ and $R^{14}$ are joined together so that $CR^4$-$CR^{14}$ is an olefinic double bond; wherein either $R^5$ is hydrogen and $R^6$ is hydrogen, methyl, ethyl or n-propyl, or $R^5$ and $R^6$ together form —CH$_2$—, —CH(CH$_3$)—, —CH$_2$CH$_2$—, —CH=CH— or —S—; wherein the aromatic rings B and C either bear no further substitutent or bear one or more fluoro, methyl or ethyl substituents;

wherein the group -A- has the formula $$-A^1-Y^3-A^{21}-$$

wherein $A^1$ is straight-chain alkylene or alkenylene each of 2 to 9 carbon atoms, $A^{21}$ is a direct link, methylene, ethylene, trimethylene or vinylene, and -Y$^3$- is a mono- or bi-cyclic divalent heterocyclene consisting of at least one 5-membered heterocyclic ring having two ring nitrogen atoms, which ring may be fused to a benzene ring;

wherein X is —CONR$^2$—, —S—, —SO— or —SO$_2$—;

wherein either $R^1$ is methyl, ethyl, n-propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, n-undecyl, allyl, cyclopentyl, cyclohexyl, phenyl, o-ethylphenyl, p-chlorophenyl, m-chlorophenyl, p-cyanophenyl, p-hydroxyphenyl, p-methoxyphenyl, benzyl, alpha-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl, p-chlorophenethyl, 2-chloro-2,2-difluoro-ethyl, 2,2,2-trifluoroethyl, 1H,1H-heptafluorobutyl, 4,4,5,5,5-pentafluoropentyl or 1H,1H,2H,2H,3H,3H-heptafluorohexyl and $R^2$ is hydrogen, methyl, ethyl or n-butyl, or —NR$^1$R$^2$ is pyrrolidino, piperidino, 4-methylpiperidino, 3-methylpiperidino, morpholino or 4-methylpiperazino; or a salt thereof.

3. A phenol derivative as claimed in claim 1 wherein $R^{15}$, $R^{23}$ and $R^{43}$ are all hydrogen, wherein $R^{13}$ and $R^{33}$ both have the formula R$^3$O- wherein $R^{13}$ is hydrogen, wherein either $R^4$ is hydrogen and $R^{14}$ is hydrogen, methyl or ethyl, or $R^4$ and $R^{14}$ are joined together, wherein either $R^5$ is hydrogen and $R^6$ is methyl, ethyl or n-propyl, or $R^5$ and $R^6$ together form —CH$_2$—, —CH$_2$CH$_2$—, —CH(CH$_3$)—, —CH=CH— or —S—, wherein —A— is $$-(CH_2)_p-Y^3-(CH_2)_q-$$

wherein p is an integer from 2 to 9, q is 0 to 3, and $Y^3$ is pyrazol-1,4-ylene or 1,3,4-oxadiazol-2,5-ylene wherein $R^1$ is alkyl or fluoroalkyl each of 4 to 10 carbon atoms, or phenyl or chlorophenyl,or alkyl of 1 to 3 carbon atoms which bears a phenyl, tolyl, halogenophenyl or trifluoromethylphenyl substituent, or is linked to $R^2$ as stated below; wherein X is —CONR$^2$—, —S—, —SO— or —SO$_2$—, wherein $R^2$ is hydrogen or alkyl of up to 3 carbon atoms or together with $R^1$ forms alkylene of 5 or 6 carbon atoms; and wherein ring C may optionally bear one or two methyl substituents.

4. A phenol derivative as claimed in claim 1 wherein the number of carbon atoms in the two groups A (excluding those in the heterocylene group $Y^3$) and $R^1$ adds up to 11 to 13 if there is no phenyl group in $R^1$, and 13 to 15 if there is a phenyl group in $R^1$.

5. A phenol derivative as claimed in claim 1 wherein: NU is 6-hydroxy-2-p-hydroxyphenylnaphth-1-yl and A is —(CH$_2$)$_5$—Y$^3$—(CH$_2$)$_2$—;

or NU is 1,2,3,4-tetrahydro-6-hydroxy-2-p-hydroxyphenylnaphthyl-1-yl (either 1RS, 2RS or 1RS, 2SR isomer), or 1,2,3,4-tetrahydro-6-hydroxy-2-p-hydroxyphenyl-2-methylnaphth-1-yl (either 1RS, 2RS or 1RS, 2SR isomer), and A is —(CH$_2$)$_4$—Y$^3$—(CH$_2$)$_2$— or —(CH$_2$)$_4$—Y$^3$—(CH$_2$)$_3$—;

or NU is (1RS, 2RS)-5-hydroxy-2-p-hydroxyphenylindan-1-yl or (1RS, 2RS)-5-hydroxy-2-p-hydroxyphenyl-2-methylindan-1-yl and A is —(CH$_2$)$_4$—Y$^3$—(CH$_2$)$_2$—;

wherein —Y$^3$— is pyrazol-1,4-ylene, or 1,3,4-oxadiazol-2,5-ylene, and wherein xR$^1$ is —CONR$^1$R$^2$ wherein R$^2$ is hydrogen or methyl and R$^1$ is n-butyl, 1H,1H-heptafluorobutyl, n-pentyl or n-hexyl, or XR$^1$ is —SR$^1$, SOR$^1$ or —SO$_2$R$^1$ wherein R$^1$ is n-penytyl, n-hexyl, 4,4,5,5,5-penta-fluoropentyl or 1H,1H,2H,2H,3H,3H-heptafluorohexyl.

6. A phenol derivative of the formula:

$$NU-A-X-R^1$$

wherein NU is (1RS, 2RS)-1,2,3,4-tetrahydro-6-hydroxy-2-p-hydroxyphenyl-2-methylnaphth-1-yl and A is —(CH$_2$)$_4$—Y$^3$—(CH$_2$)$_2$— or —(CH$_2$)$_4$—Y$^3$—(CH$_2$)$_3$—;

wherein $Y^3$ is pyrazol-1,4-ylene; and wherein XR$^1$ is —CONR$^1$R$^2$ wherein R$^2$ is hydrogen or methyl and R$^1$ is n-butyl, 1H, 1H-heptafluorobutyl, n-pentyl or n-hexyl, or XR$^1$ is —SR$^1$, SOR$^1$ or —SO$_2$R$^1$ wherein R$^1$ is n-pentyl, n-hexyl, 4,4,5,5,5-penta-fluoropentyl or 1H,1H,2H,2H,3H,3H-heptafluorohexyl.

7. The compound: (1RS,2RS)-1-{4-[4-(2-n-hexylthioethyl)pyrazol-1-yl]-butyl}-2-p-hydroxyphenyl-2-methyl-1,2,3,4-tetrahydronaphth-6-ol or the corresponding hexylsulphinyl derivative, or the corresponding 4,4,5,5,5-pentafluoropentylthio derivative, or the corresponding 4,4,5,5,5-pentafluoropentylsulphinyl derivative.

8. A pharmaceutical composition having antiestrogenic activity comprising an amount of a phenol derivative, claimed in claim 1, sufficient to exert an antioestrogenic effect, with a pharmaceutically acceptable diluent or carrier.

9. A method for producing an antioestrogenic effect in a warm-blooded animal in need of such treatment, which comprises administering to said animal an effective amount of at least one phenol derivative as claimed in claim 1.

* * * * *